US012714575B2

(12) United States Patent
Eggli et al.

(10) Patent No.: US 12,714,575 B2
(45) Date of Patent: Aug. 25, 2026

(54) BONE PLUG INSERTION INSTRUMENT

(71) Applicant: Stefan Eggli, Pierrafortscha (CH)

(72) Inventors: Stefan Eggli, Pierrafortscha (CH); Janosch Häberli, Bern (CH); Tom Overes, Attiswil (CH)

(73) Assignee: Stefan Eggli, Pierrafortscha (CH)

( * ) Notice: Subject to any disclaimer, the term of this patent is extended or adjusted under 35 U.S.C. 154(b) by 284 days.

(21) Appl. No.: 18/271,841

(22) PCT Filed: Dec. 20, 2021

(86) PCT No.: PCT/IB2021/062002
§ 371 (c)(1),
(2) Date: Jul. 11, 2023

(87) PCT Pub. No.: WO2022/153115
PCT Pub. Date: Jul. 21, 2022

(65) Prior Publication Data

US 2024/0065855 A1 Feb. 29, 2024

(30) Foreign Application Priority Data

Jan. 15, 2021 (CH) ................................ CH00035/21

(51) Int. Cl.
*A61F 2/46* (2006.01)
*A61B 17/16* (2006.01)
*A61F 2/30* (2006.01)

(52) U.S. Cl.
CPC ........ *A61F 2/4601* (2013.01); *A61B 17/1635* (2013.01); *A61F 2/30749* (2013.01);
(Continued)

(58) Field of Classification Search
CPC ...... A61F 2/4601; A61F 2/461; A61F 2/4644; A61F 17/1635
See application file for complete search history.

(56) References Cited

U.S. PATENT DOCUMENTS 5,772,664 A * 6/1998 DeSatnick ......... A61B 17/1637 606/80
5,904,685 A * 5/1999 Walawalkar .......... A61F 2/0805 606/104

(Continued)

FOREIGN PATENT DOCUMENTS

EP 0995402 A2 4/2000
WO WO2010040076 A2 4/2010
WO WO2016161026 A1 10/2016

*Primary Examiner* — Matthew J Lawson
(74) *Attorney, Agent, or Firm* — Gallium Law; Jacob Panangat; Isabel Fox

(57) ABSTRACT

A bone plug insertion instrument (1) is proposed for inserting a bone plug (70) into a target bone tunnel. The bone plug insertion instrument (1) comprises (a) an elongated housing (10) defining a first central axis, and comprising an at least partially tube-shaped insertion portion, and a handling portion, the at least partially tube-shaped insertion portion (11) defining, substantially orthogonally to the first central axis, an inner cross-sectional area at least partially surrounded by a bone engaging end surface of the at least partially tube-shaped insertion portion; and (b) an elongated plunger (40) comprising an actuating portion and a bone plug driving portion with a bone plug engaging end surface (43) having an engaging area of 20% to 80% of the inner cross-sectional area. The elongated plunger (40) is configured to move relative to the elongated housing (10) between a first position and a second, different position.

17 Claims, 7 Drawing Sheets

(52) U.S. Cl.
CPC ............ *A61F 2/461* (2013.01); *A61F 2/4644* (2013.01); *A61F 2220/0008* (2013.01)

(56) References Cited

U.S. PATENT DOCUMENTS

| | | | | |
|---|---|---|---|---|
| 6,579,295 | B1 | 6/2003 | Supinski | |
| 6,582,438 | B2 * | 6/2003 | DeMayo | A61B 17/8819 606/92 |
| 8,435,305 | B2 * | 5/2013 | Lozier | A61F 2/28 606/86 R |
| 2003/0236573 | A1 | 12/2003 | Evans et al. | |
| 2004/0267276 | A1 | 12/2004 | Camino et al. | |
| 2006/0084992 | A1 * | 4/2006 | Michelson | A61B 17/1757 606/86 R |
| 2006/0178748 | A1 * | 8/2006 | Dinger, III | A61B 17/1615 623/18.11 |
| 2007/0043376 | A1 * | 2/2007 | Leatherbury | A61F 2/4601 606/99 |
| 2009/0054906 | A1 * | 2/2009 | Walthall | A61F 2/4618 606/108 |
| 2009/0105712 | A1 | 4/2009 | Dauster et al. | |
| 2010/0292704 | A1 * | 11/2010 | Stoffel | A61F 2/4601 606/99 |
| 2012/0053642 | A1 | 3/2012 | Lozier et al. | |
| 2014/0324169 | A1 * | 10/2014 | Maher | A61F 2/442 264/28 |
| 2017/0340455 | A1 * | 11/2017 | Greter | A61B 17/8833 |
| 2021/0267769 | A1 * | 9/2021 | Kohler | A61B 17/92 |

* cited by examiner 10
27

15
CSA
13/31
IC1/IVC1
14
24

29/34
16
19/23
11
25
12
A1
α

70
30
X 74
13
43
73
X

BONE PLUG INSERTION INSTRUMENT

TECHNICAL FIELD OF THE INVENTION

The present invention relates to a bone plug insertion instrument for introducing a bone plug into a target bone tunnel in a distal femoral bone. The invention also relates to a method of operating the bone plug insertion instrument.

BACKGROUND OF THE INVENTION

In orthopaedic interventions around a knee, soft tissue grafts are often retrieved from a harvesting site and transferred to a target site. An example surgical intervention process for such a transplantation is the anterior cruciate ligament (ACL) reconstruction process, during which autologous tissues, such as tendons and ligaments, are used. One example technique for ACL reconstruction uses a quadriceps tendon and a patellar bone plug in the reconstruction process. This arthroscopically performed surgery includes the following procedures.

Procedure 1: Quadriceps Tendon Graft Harvesting and Reinforcement Thereof.

A central piece of the quadriceps tendon graft having a length of e.g. approximately 5 cm including an attached proximal patellar bone plug having a length of e.g. approximately 2 cm is harvested. This graft will serve as a replacement for the torn anterior cruciate ligament. The tendon portion of the graft is reinforced with suture. This suture allows the surgeon to correctly tension and fixate the graft to the tibial bone, as described in greater detail later.

To harvest a bone plug from the patellar bone, most often a hollow drill is used. A hollow drill has a thin wall thickness and allows an intact bone plug to be drilled out, which is only minimally smaller than the hole or tunnel created by the drill. These bone plugs typically have an outer diameter of 8-12 mm and a length of 10-25 mm. Specifically, when retrieving a patellar bone plug using a hollow drill, the plug is retrieved from the top side of the patella, flush with the outer face of the bone. After drilling for example to a depth of 20 mm, a chisel is used to cut of the bone plug at its far end.

Procedure 2: Tibial Tunnel Creation

A tunnel is drilled from the anterior and proximal tibia towards the natural tibial foot-print of the ACL. Preferably, a hollow drill is used in order to retrieve a bone plug, which can be placed back in the tibial tunnel, at a later step during the surgery. The tibial tunnel is shaped as a through bore having of a diameter of approximately 10 mm.

Procedure 3: Femoral Tunnel Preparation

A guide wire is placed through a femoral bone, defining the intended anatomical direction of a femoral tunnel. The guide wire is advanced through the bone and made to exit at the antero-lateral side of the leg. The guidewire comprises an eyelet, used to pass a suture string throughout the femur in a following procedural step. Using a cannulated drill, the guide wire is over-drilled and the tunnel is created. Alternatively the femoral tunnel is created using a punching instrument. The femoral tunnel is shaped as a blind hole having a diameter of approximately 8-10 mm and a length of approximately 20-25 mm.

Procedure 4: Graft Placement/ACL Reconstruction

The patellar bone plug including the quadriceps tendon as retrieved in procedure 1 is impacted into the femoral tunnel. This press-fit fixation will hold the bone plug in place during the healing period. The bone plug will osseointegrate with the surrounding femoral bone.

To achieve the press-fit fixation, most often the tip of the cylindrical graft, i.e. the bone plug, is given a conical tip, using cutting pliers, or a bone plug compression instrument. The conical tip, which extends over approximately one third of the bone plug length, will facilitate insertion of the bone plug into the femoral tunnel. Typically the reshaped tip has an outer circumference which is smaller than the entry circumference of the femoral tunnel. Furthermore, to facilitate the insertion, in a next step, a bore is drilled into the bone plug, and a suture strand is looped through the bore. This suture strand is looped through the eyelet of the earlier placed femoral guide wire and is pulled through the femoral bone and pulled through the patient's muscles and skin and exits at the antero-lateral side of the leg. This suture strand is used to pull the bone plug into the femoral tunnel. Additionally the suture strand helps to align the bone plug with the femoral tunnel. Now, by pulling the suture strand and by tapping against the bone plug using a plunger and a mallet, the bone plug is brought in place.

In a next step, the quadriceps tendon graft is pulled over the joint space, and fixated in the tibial tunnel. Most commonly the tibial fixation may be carried out using a screw for suture attachment or an interference screw. A screw for suture attachment would be placed on the anterior side of the tibial bone, and the suture is tied around the screw for fixation. Using an interference screw, a resorbable and thick screw is placed next to the ligament or tendon in the tibial tunnel, and it rigidly jams the tendon between the screw and the tunnel wall.

The success of the surgery greatly depends on the primary stability of the patellar bone plug in the femoral tunnel during the healing and osseointegration phase.

Currently, as described, by pulling the suture strand and by tapping against the bone plug using a plunger and a mallet, the bone plug is brought in place. The suture strand had to be pulled throughout the femoral bone, muscles and skin using a guide wire, to allow this procedure to be executed. This surgical step is a time-consuming step, and it causes temporarily trauma to the bone, muscle and skin.

In order to eliminate this trauma, and to reduce surgery time by reducing surgical steps, there is thus a need for an improved instrument for insertion of the bone plug that upon inserting the bone plug does not require the combined pushing (impacting) and pulling action.

SUMMARY OF THE INVENTION

It is an object of the present invention to overcome at least some of the problems associated with soft tissue graft fixation techniques, for instance in anterior cruciate ligament surgery. More specifically, an object of the present invention is to provide a medical instrument for the insertion of a bone plug that allows the bone plug to be inserted in an accurate and reproducible manner, without the need of applying pulling forces to suture strands that are passed through the bone, muscle and skin of the patient.

According to a first aspect of the invention, there is provided a bone plug insertion instrument as recited in claim 1.

The proposed novel bone plug insertion instrument has the advantage that it can efficiently be used during a surgical intervention in which a bone plug is inserted into a target hole in the femoral condyle, for instance, at the native (now torn and removed) ACL footprint site. More specifically, the bone plug insertion instrument allows a practitioner to insert a bone plug in a controlled and reproducible manner through a small antero-medial portal into the knee joint, which is commonly used for these arthroscopic reconstructive interventions. Therefore, the surgery becomes a standardised procedure providing reproducible and predictable results. Moreover, the surgery time can be reduced, and a currently commonly executed surgical step can be eliminated.

The elimination of this combined "pushing & pulling" step obviates the need for passing a guide wire throughout the whole leg, drilling of a bore into the bone plug and passing a suture therethrough, pulling the suture through the leg, removing this suture, and it further obviates the need for a costly guide wire with an eyelet.

The bone plug may be harvested using a hollow drill, circumferentially setting free the bone plug. As a result, the harvested bone plug typically has a cylindrical shape.

According to a second aspect of the invention, there is provided a kit comprising the bone plug insertion instrument and a bone plug grafting instrument.

According to a third aspect of the invention, there is provided a method of operating the bone plug insertion instrument as recited in claim 17.

Other aspects of the invention are recited in the detailed description and dependent claims attached hereto.

BRIEF DESCRIPTION OF THE DRAWINGS

Other features and advantages of the invention will become apparent from the following description of a non-limiting example embodiment, with reference to the appended drawings, in which.

DETAILED DESCRIPTION OF THE INVENTION

Figure 1A:
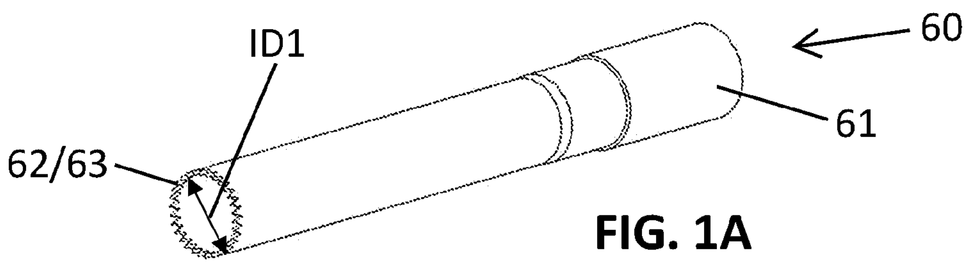
FIG. 1A illustrates in a perspective view an example bone plug grafting instrument.

An embodiment of the present invention will next be described in detail with reference to the attached figures. The embodiment is described in the context of a bone plug insertion instrument configured to insert a cylindrical bone plug into a target femoral tunnel, but the teachings of the invention are not limited to this environment. The teachings of the present invention are equally applicable to differently shaped bone plugs as well. Identical or corresponding functional and structural elements which appear in the different drawings are assigned the same reference numerals. When the word "contacting" is used, this is to be understood that a first object is configured to contact either directly or directly a second object. Similarly, when the word "engaging" is used, this is to be understood that a first object is configured to come in contact either directly or directly with a second object. Furthermore, in the present description, there is no particular difference in the meaning between these two words, unless this is implicitly or explicitly made clear in the context.

Figure 1B:
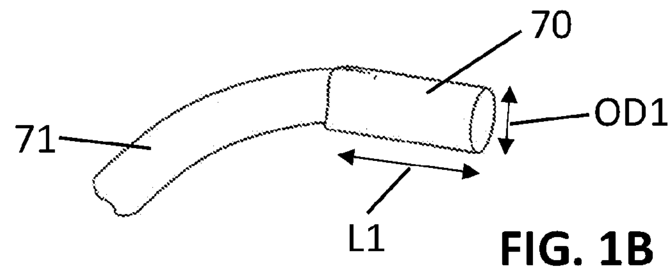
FIG. 1B illustrates an example bone plug with a tendon graft attached to it.

FIG. 1A shows an example grafting instrument 60 or a bone plug removal instrument, while FIG. 1B shows a bone plug 70 together with a tendon 71 attached to the bone plug. The grafting instrument 60 is sized and shaped as a thin-walled tube, i.e. a hollow tube thus comprising a bore or cavity extending longitudinally through it. A first end 61 of the grafting instrument is configured to be coupled to a surgical drilling machine, while a second, opposite end 62 comprises a cutting edge 63 or surface, in this example in the form of a serrated cutting surface or cutting teeth. The tube-shaped grafting instrument 60 defines a first inner diameter ID1, and is intended to graft a bone plug of a first size with a first outer diameter OD1 and length L1. The bone plug 70 with an attached tendon 71 can be grafted using the grafting instrument 60. The length L1 may be between 10 mm and 25 mm, or more specifically between 18 mm to 22 mm, while the first outer diameter OD1 may be smaller than 12 mm, or smaller than 10 mm or more specifically between 8 mm and 12 mm. In this example, the bone plug is of a substantially cylindrical shape. Thus, as shown in FIG. 1A, the grafting instrument is a hollow drill element configured to be attached to a surgical drilling machine. By means of drilling, the grafting instrument 60 is advanced forward into the target bone. The bone plug to be retrieved is thus received in the tube. Specifically, when retrieving a patellar bone plug using a hollow drill, the plug is retrieved from the top side of the patella, flush with the outer face of the bone. After drilling for example to a depth of 20 mm, a chisel is used to cut off the bone plug at its far end. The separated bone plug and tendon are located within the grafting instrument.

Figure 2A:
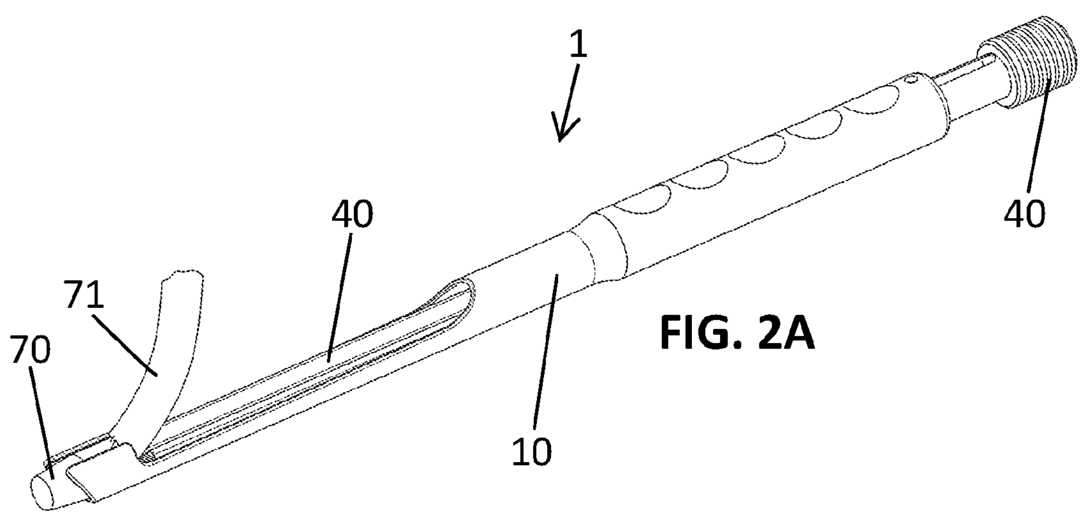
FIGS. 2A and 2B illustrate in perspective views an example bone plug insertion instrument and a bone plug with a tendon attached to it.
Figure 2B:
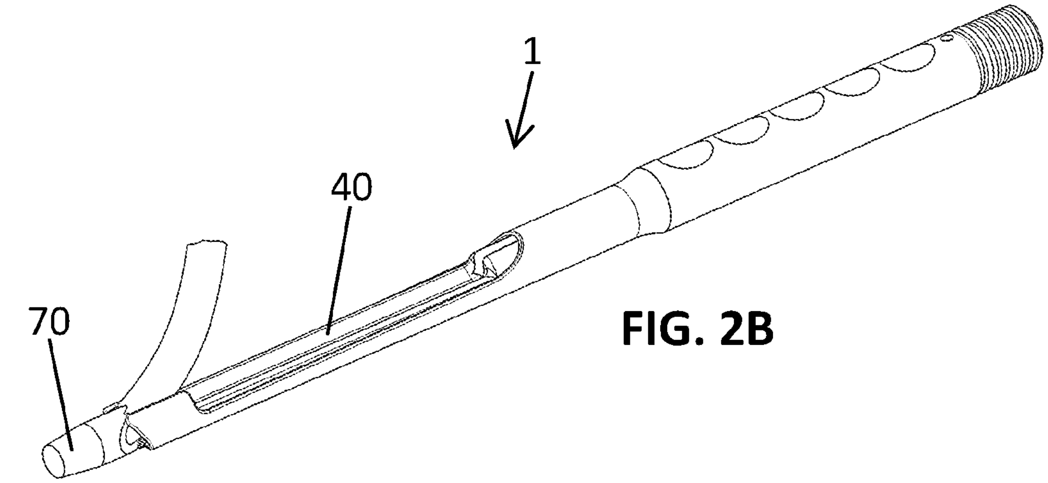

FIGS. 2A and 2B show an example bone insertion instrument 1 or bone plug insertion instrument and the individual components. The bone plug insertion instrument comprises an elongated housing 10 or body element and an elongated plunger 40. A bone plug 70 with an attached tendon 71 is also shown. In FIG. 2A, the bone plug 70 is engaged or received in the bone plug insertion instrument, while FIG. 2B shows a situation where the bone plug has been ejected or expelled out of the bone plug insertion instrument 1.

Figures 3A, 3B, 3C:
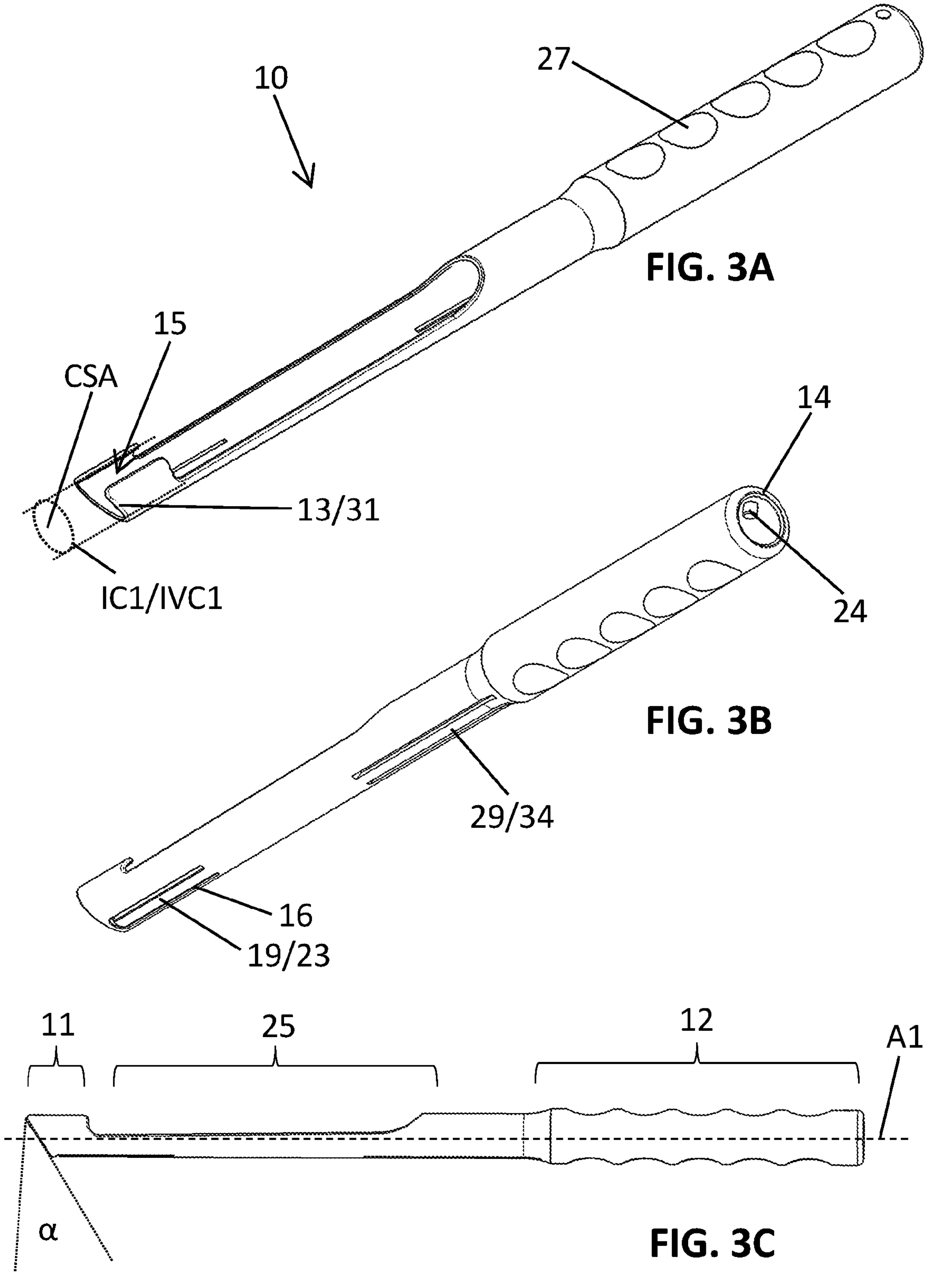
FIGS. 3A to 3C show in different views a first component, namely an elongated housing, of the bone plug insertion instrument according to an example of the present invention.

FIGS. 3A to 3C depict the elongated housing in greater detail. The elongated housing 10 comprises an at least partially tube-shaped insertion portion 11, a middle portion 25, and a handling portion 12. The at least partially tube-shaped insertion portion 11 is a hollow element sized and shaped to hold the bone plug 70 with an attached tendon 71. The handling portion 12 allows the user to manipulate the bone plug insertion instrument 1, and the middle portion 25 separates the handling and insertion portions in such a manner that the bone plug can be placed by means of arthroscopic surgery. In 35 this example, the middle portion is shaped as a partial tube, such as half a tube, i.e. a tube which longitudinally comprises one or more open or exposed sides. The partial tube will allow placement of the bone plug into the insertion portion 11. Furthermore, in this example, the handling portion is formed as an elongated grip 27.

In this example, the at least partially tube-shaped insertion portion 11 is substantially rotationally symmetric and has substantially circular circumference IC1 or inner virtual circular circumference IVC1, which is substantially equally sized as the first outer diameter OD1 of the bone plug. The inner circumference IC1 or inner virtual circular circumference IVC1 defines a cross-sectional area CSA measured orthogonally or substantially orthogonally to a longitudinal axis of the bone plug insertion instrument.

It is to be noted that in the present description, the word circumference is used to describe the boundary of a curved geometric figure or object. More specifically, the word inner circumference may be used to describe the circular inner boundary of a cylinder. Although in the present example, the tube is of a cylindrical shape, the word circumference is not limited to a circular boundary, but it also defines a general distance inside an object, such as an inner perimeter, border, boundary, periphery, etc. For instance, according to an example, the word circumference may describe the boundary of an element having an oval shape. Other shapes such as polygons, irregular shapes also have an (average) internal boundary forming a circumference.

The cross-sectional area CSA is at least partially defined or surrounded by a bone contacting or engaging end surface 13 (or a target bone contacting end surface or a first contact surface) and optionally by its virtual extension if the bone engaging end surface 13 is not a closed surface (where the virtual extension would close the non-closed bone engaging end surface). The bone engaging end surface 13 forms the tip 31 or distal end of the insertion instrument 1 and is configured to be pressed against the bone (in this example the lateral inner side of the intercondylar notch of a femoral bone), which directly surrounds the target femoral tunnel 80 (see FIG. 5D). The elongated housing 10 further comprises or defines a first central axis A1 coinciding with the longitudinal axis of the insertion instrument 1. In this example, the bone engaging end surface 13 is oriented at an acute angle α to the first central axis A1 and it has an overall planar shape. Alternatively, the bone engaging end surface 13 may be arranged perpendicularly to the first central axis A1 as depicted in FIG. 6G.

The at least partially tube-shaped insertion portion 11 comprises a clearance or opening, more specifically a soft-tissue graft clearance 15, which intersects with the bone engaging end surface 13. This soft-tissue graft clearance forms a passage for the tendon 71 of the graft to pass through, when the bone plug is inserted into the femoral tunnel. The size and shape of the soft-tissue graft clearance prevent the tendon 71 from getting damaged when the bone plug 70 is advanced forward out of the elongated housing, as described in greater detail later. The at least partially tube-shaped insertion portion 11 may thus be understood to be a tube or cylinder with a slot longitudinally through the tube outer wall.

For holding or clamping purposes of the bone plug 70 (and tendon), the at least partially tube-shaped insertion portion 11 comprises a first slot 16, in this example a U-shaped slot, that forms a first compliance structure 19, such as a leaf spring 23, to hold or clamp the bone plug. Thus, the first compliance structure forms a first elastic structure. In this example, the first slot 16 is located on a side of the housing 10 that is opposite to the side where the graft clearance 15 is located. In its rest state, the leaf spring is bent inwards (i.e. towards the centre of the housing) and therefore it presses the bone plug against the inner walls of the tube-shaped insertion portion 11, and so inhibits an unwanted early release of the bone plug.

In this example, the handling portion 12 comprises an inwardly directed (i.e. in this example towards the first central axis A1) rotation-inhibiting protrusion 24. As described later, this protrusion is configured to engage with an elongated channel, groove or track 45 of the elongated plunger 40. This track is configured to receive the rotation-inhibiting protrusion 24 in an substantially play free manner and so only allowing a translational motion of the plunger (with respect to the housing), where the direction of the motion is parallel to the first central axis A1.

As described later, the insertion instrument will most often, during operation, follow an oblique direction, i.e. an upwards-oriented direction. The bone plug is placed into the elongated tube (i.e. the tube-shaped insertion portion 11), and the handling portion is then held by one hand of the operator or surgeon. The other hand can in this way hold a mallet or small hammer to tap onto the elongated plunger. In order to prevent the plunger from disengaging unwantedly out of the elongated housing, the elongated housing 10 comprises a friction mechanism 29 (which may also be understood as a compliance structure), which inhibits unwanted motion of the plunger in relation to the housing. In this example, the friction mechanism 29 is formed as an inwardly bent second leaf spring 34. Alternatively, the plunger may comprise the friction mechanism. To limit the amount of translation of the elongated plunger in relation to the elongated housing, the elongated housing comprises a first stop seat 14, which is configured to engage with a second stop seat 44 of the elongated plunger as described in greater detail later.

Figures 4A, 4B:
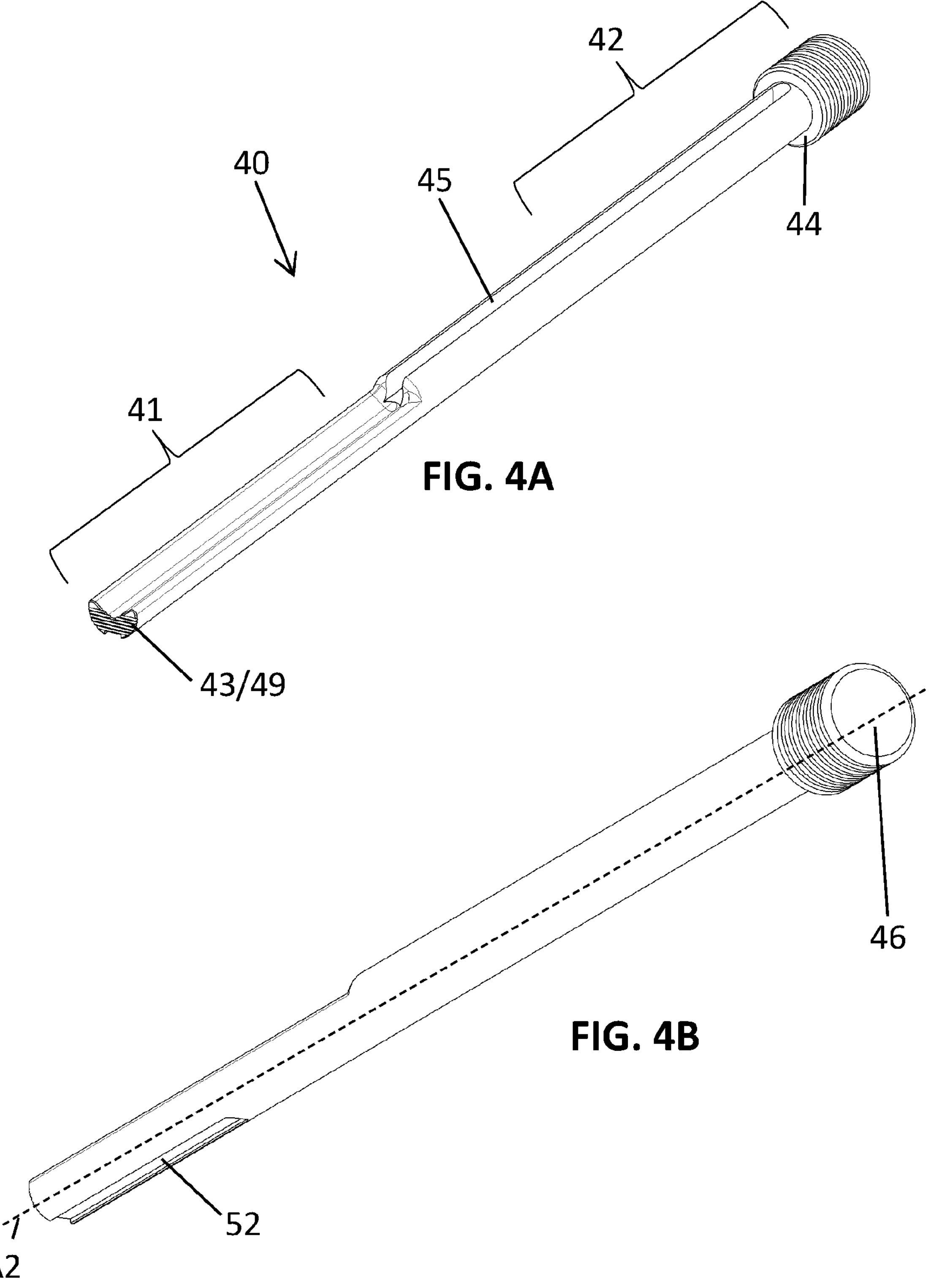
FIGS. 4A and 4B show in different views a second component, namely an elongated plunger, of the bone plug insertion instrument according to an example of the present invention.

FIGS. 4A to 4B show the elongated plunger or pusher in greater detail. In this example, the plunger is to be understood as an element that is configured to move at least between a first position and a second position with respect to the elongated housing, and where in the second position, the plunger is configured to expulse or remove the bone plug out of the insertion instrument. The movement is in this example a sliding movement. The plunger may then return to the first position to be used again. The elongated plunger 40 comprises a bone plug driving portion 41 with a bone plug contacting or engaging end surface 43 (or a second contact surface). At the opposite end (i.e. at the proximal end), the elongated plunger comprises an actuating portion 42. The actuating portion ends in an impaction end 46 comprising an impaction surface. The elongated plunger comprises or defines a second central axis A2 along the length of the elongated plunger. The bone plug driving portion 41 is sized and shaped to fit (axially) in the at least partially tube-shaped insertion portion 11. In this example, the bone plug driving portion 41 has a substantially cross-sectional crescent shape and is sized and shaped to overlap partially with the inner cross-sectional area CSA. More specifically, according to the present example, the cross section (orthogonally to the second central axis A2) of the bone plug driving portion 41 is sized and shaped such that its area is 10% to 90% of the inner cross-sectional area CSA, which defines a footprint or virtual footprint of the bone engaging end surface 13. In other words, the surface or contact area of the bone plug engaging end surface 43 is 10% to 90% of the size of the inner cross-sectional area CSA. However, the likelihood for a good outcome would be relatively high if the surface or contact area of the bone plug engaging end surface 43 is 20% to 80% of the size of the inner cross-sectional area CSA. The tendon 71 is attached to one end of the bone plug 70. This attachment area or footprint of the tendon covers the majority of the bone plug end. As described later, upon insertion of the bone plug, a tapping force is applied to this attachment area by the driving portion 41. Ideally, the majority of these forces is transferred directly to the bone, to inhibit damage of the tendon footprint. A damage could negatively influence the overall strength of the tendon. If the bone plug engaging end surface is too small, then too high pressure would be exerted on the bone plug and/or tendon. The bone would be crushed and/or the tendon mashed, or the end surface would slide off. On the other hand, if the bone plug engaging end surface is too big, then a large part of the footprint of the tendon would be mashed. The fibres would be damaged and there is a high risk that the tendon would be ruptured later. In the present example, the bone plug engaging end surface 43 comprises grooves 49 or a textured or rough surface, to increase friction between the bone plug 70 and the bone plug engaging end surface 43. In this manner, the grip of the target impaction area of the bone plug 70 can be increased. In this case, the elongated plunger further comprises an elongated recess 52 at its bottom side. The advantage of this recess is overcome the first compliance structure 19. In this manner, the movement of the elongated plunger is not hindered by the first compliance structure.

As described earlier, the elongated plunger 40 comprises an elongated track 45, which is sized and shaped to receive the rotation-inhibiting protrusion 24. The elongated track 45 is oriented parallel or substantially parallel to the second central axis A2. The engagement of the protrusion in the track inhibits rotation of the elongated protrusion about the second central axis A2. Furthermore, the elongated plunger comprises a second stop seat 44, which is intended to engage with the first stop seat to limit the maximal insertion depth of the elongated plunger 40 within the housing 10.

FIGS. 5A to 5H illustrate the method of operating the bone plug insertion instrument 1, and they show further example details of the components of the bone plug insertion instrument 1 and their interaction.

The elongated plunger 40 is configured to move relative to the elongated housing 10 between a first position and a second, different position wherein in the first position, the bone plug insertion instrument 10 forms an open configuration, and in the second position, the bone plug insertion instrument 10 forms a substantially closed configuration.

Figures 5A, 5B, 5C:
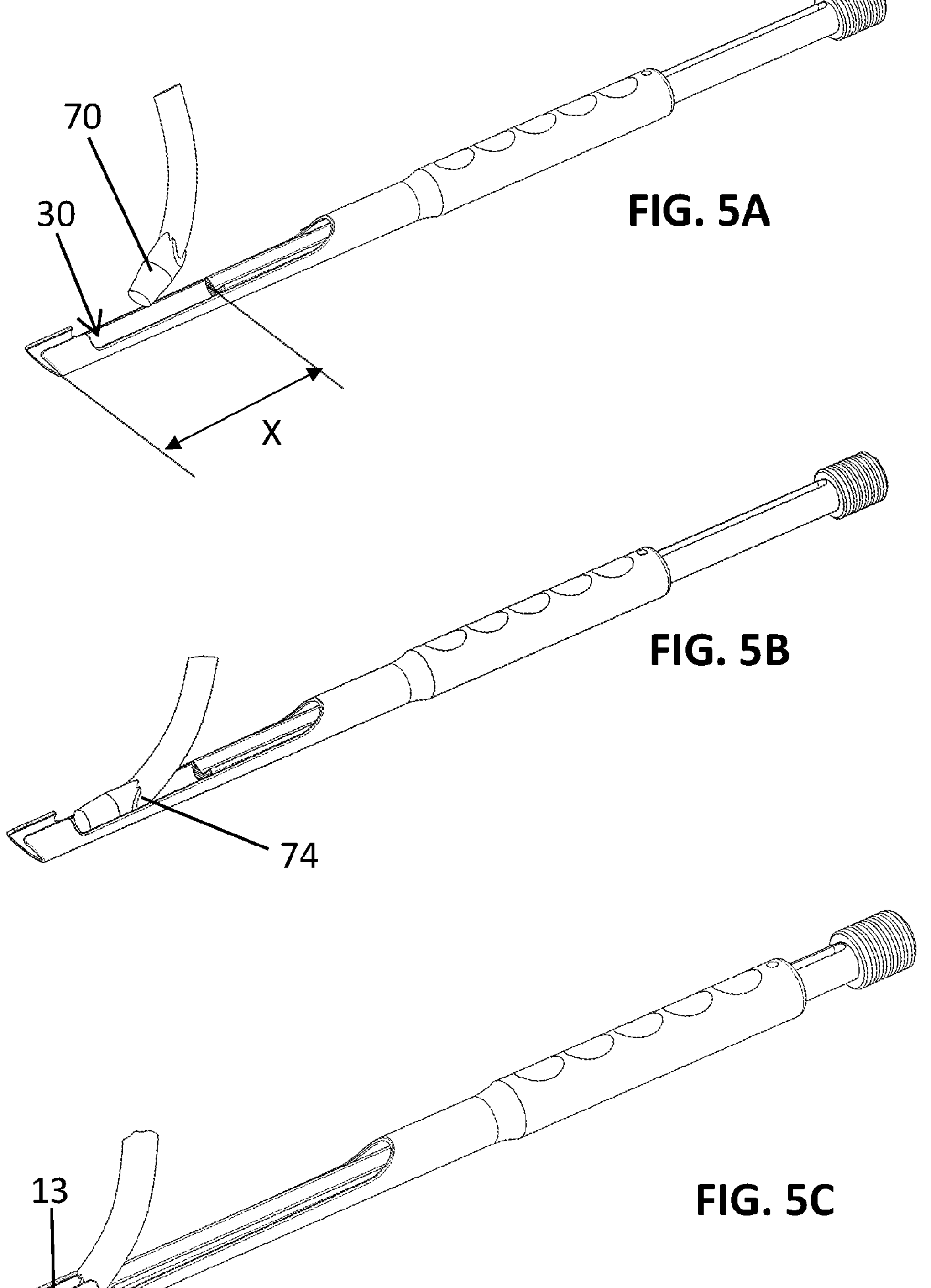
FIGS. 5A to 5H illustrate the operating procedure of the bone plug insertion instrument.

FIGS. 5A and 5B show the first position. In the first position, the elongated housing 10 and the elongated plunger 40 are shifted longitudinally or lengthwise by a distance X (a first distance) in relation to each other providing the possibility for the bone plug 70 to be arranged in a space 30 inside the tube-shaped insertion portion 11 between the bone engaging end surface 13 and the bone plug engaging end surface 43. The distance X is here measured as the separation between the bone engaging end surface 13 and the bone plug engaging end surface 43, for example along an imaginary line, which is parallel to the first or second central axis.

FIG. 5C shows how the bone plug engaging end surface 43 is being engaged against or with the bone plug rear end 74. The distance X is now reduced. In this example, the bone plug tip 73 protrudes beyond the bone engaging end surface 13.

Figure 5D:
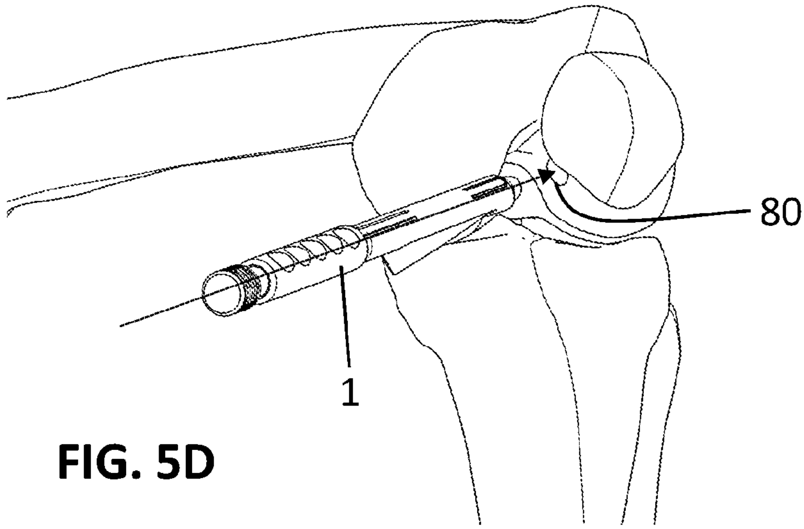
Figures 6A, 6B, 6C, 6D, 6E, 6F, 6G:
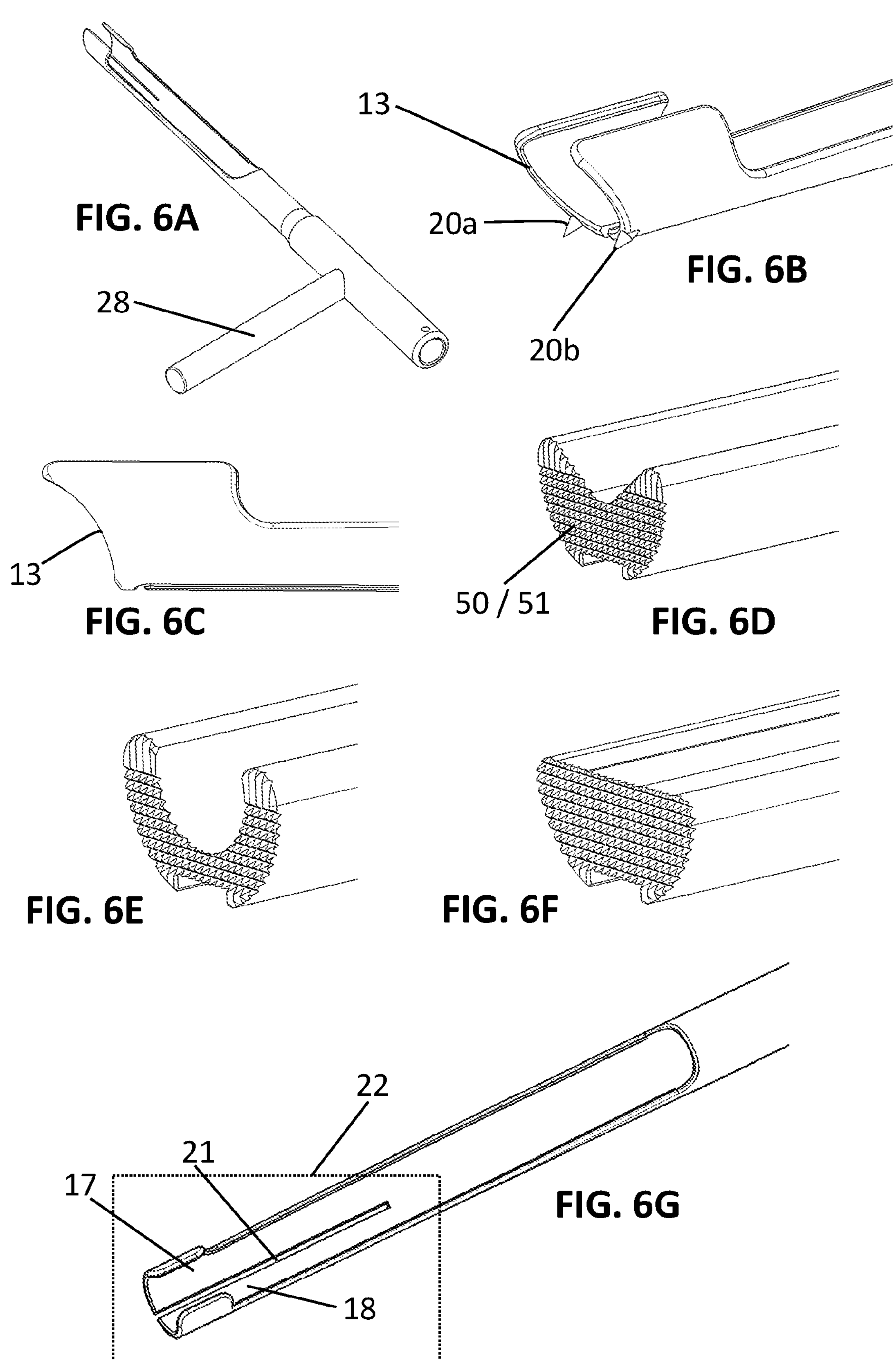
FIGS. 6A to 6G show alternative variants of the bone plug insertion instrument.

FIG. 5D shows the bone plug insertion instrument including the bone plug and tendon being aligned with the target femoral bone tunnel 80. In an example scenario, the bone plug insertion instrument is introduced into the knee joint through a so-called antero-medial portal.

Figure 5E:
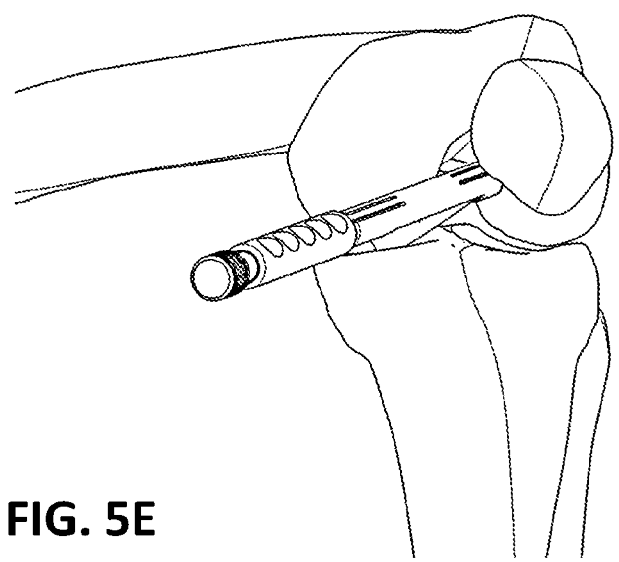

FIG. 5E shows the engagement of the bone engaging end surface 13 with the target bone and the bone plug tip 73 being engaged with or partially inserted in the femoral bone tunnel.

Figures 5F, 5G, 5H:
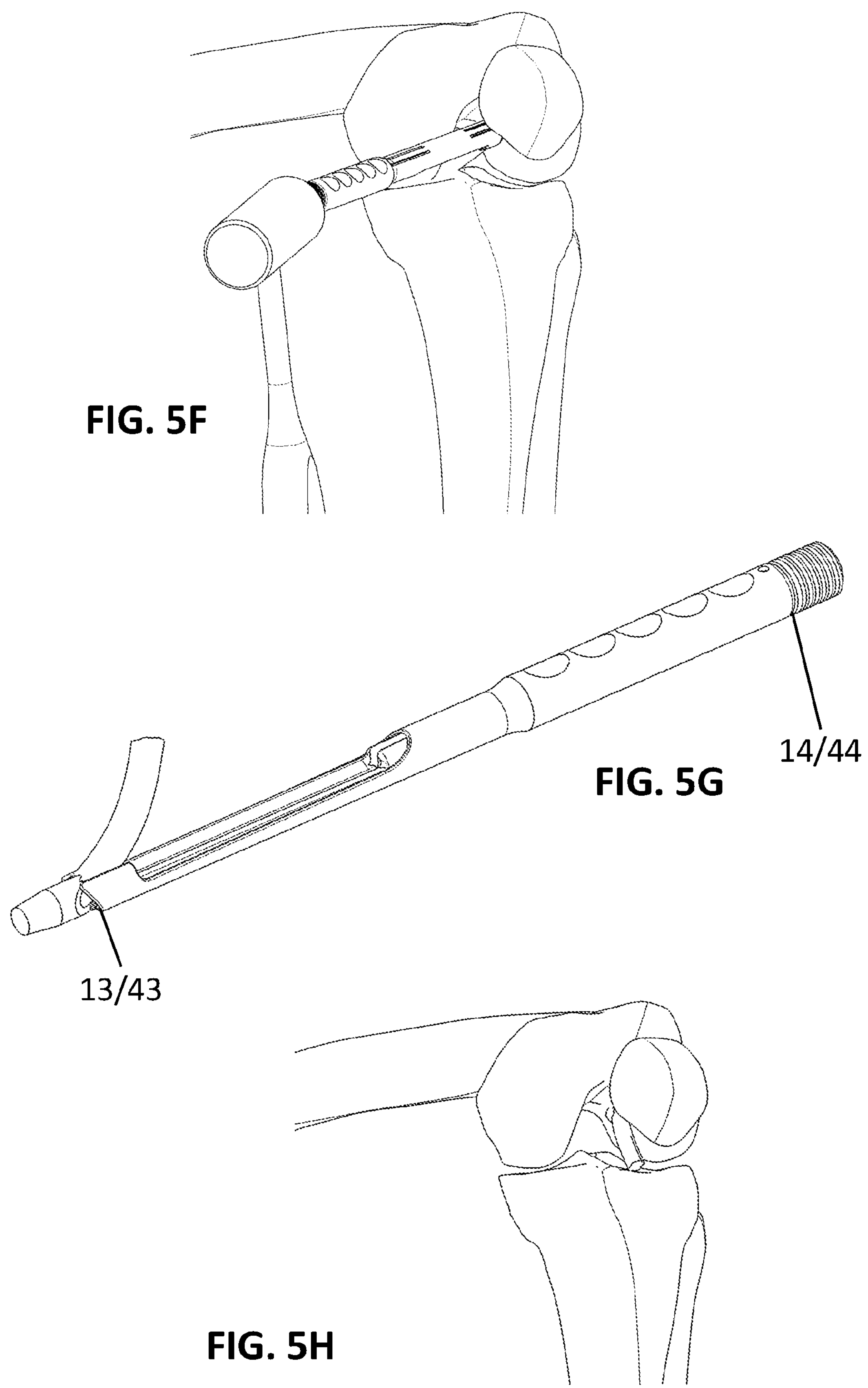

FIGS. 5F and 5G (without the target bone) show that by exerting force or impulses to the actuating portion 42, the bone plug is ejected from the insertion instrument into the target femoral tunnel. The elongated plunger 40 has now reached the second position.

In the second position, the bone plug insertion instrument 10 forms a substantially closed configuration, in which the space 30 is reduced in size in such a manner that the end surface 13 and the bone plug engaging end surface 43 are overlapping or arranged adjacently. In other words, the distance X (a second distance) has been reduced to zero or approximately zero. In this example the distance X in the second position is less than 1 cm or more specifically less than 0.5 cm, for example substantially 0 cm. It is to be noted that this distance may even become negative. This would happen if the bone plug engaging end surface 43 has moved beyond the bone engaging end surface 13. In this example, the elongated housing 10 comprises a first stop seat 14 and the elongated plunger 40 comprises a second stop seat 44, and in the second position, the first and second stop seats 14, 44 are engaged with each other or adjacently arranged. In other words, now the first and second stop seats are in contact with each other or rest against each other. The first and second stop seats prevent the bone plug from being impacted too deep into the target bone tunnel.

FIG. 5H shows the implanted bone and tendon graft after removal of the bone plug insertion instrument.

FIGS. 6A to 6G show variants of specific aspects of the bone plug insertion instrument. FIG. 6A shows a variant according to which the handling portion 12 comprises a handle 28, which is angled with respect to the first central axis A1. Depending on the operator's preference, an angled handle may be considered more ergonomic to hold the device.

FIG. 6B shows a variant where the bone engaging end surface 13 comprises at least one spike 20*a*, 20*b*. The spike can be pressed into the target bone, and in this manner, the instrument can be stabilised.

FIG. 6C shows a variant where the bone engaging end surface 13 is non-planar, and thus has a hollow shape. In other words, the bone engaging end surface has a concave or substantially concave side profile. This kind of surface shape may improve engagement against the target bone.

FIG. 6D shows a variant where the bone plug driving portion 41 comprises pointy protrusions 50 or pyramids 51, which may be understood to form a rough or textured contact surface. This kind of configuration increases the grip of the target impaction area of the bone plug 70. The rough surface could also comprise a sandpaper-like structure.

FIG. 6E shows a variant where the bone plug driving portion 41 has a C-shaped or U-shaped cross section.

FIG. 6F shows a variant according to which the bone plug driving portion 41 has a cross section of a semi-circular shape.

FIG. 6G shows a variant designed to better hold the bone plug in place, prior to willingly ejecting the bone plug out of the bone plug insertion instrument. In this example, the elongated housing 10 comprises a second slot 21 that intersects with or reaches the bone engaging end surface 13. The second slot 21 thus extends from the bone engaging surface, in this example parallel or substantially parallel to the first central axis A1, a certain distance towards the opposite end of the insertion instrument. This slot divides the at least partially tube-shaped insertion portion 11 into a first tube section 17 and a second tube section 18, and it provides certain elasticity between these sections and so forms a second compliance structure 22, which may be understood as a second elastic structure. In this example, the at least partially tube-shaped insertion portion 11 has an inner circular circumference IC1 or inner virtual circular circumference IVC1 which is equal to or smaller than the first outer diameter OD1 of the bone plug. Thanks to the elasticity provided by the second compliance structure, a friction force can be applied to the bone plug in order to prevent an unwanted release of the bone plug 70 from the insertion instrument 1.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims. Further embodiments may be obtained by combining any of the above teachings.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A bone plug insertion instrument for inserting a bone plug into a target bone tunnel, the bone plug insertion instrument comprising:

an elongated housing defining a first central axis, and comprising an at least partially tube-shaped insertion portion, and a handling portion, the at least partially tube-shaped insertion portion defining, substantially orthogonally to the first central axis, an inner cross-sectional area at least partially surrounded by a bone contacting end surface of the at least partially tube-shaped insertion portion; and an elongated plunger comprising an actuating portion and a bone plug driving portion with a bone plug contacting end surface having a contact area of 10% to 90% of the inner cross-sectional area, the elongated plunger being configured to move relative to the elongated housing between a first position and a second, different position, wherein in the first position the bone plug insertion instrument forms an open configuration, in which the bone contacting end surface and the bone plug contacting end surface are separated by a first distance, thereby allowing the bone plug to be received in a space within the at least partially tube-shaped insertion portion between the bone contacting end surface and the bone plug contacting end surface, wherein in the second position, the bone plug insertion instrument forms a substantially closed configuration, in which a second distance between the bone contacting end surface and the bone plug contacting end surface is smaller than the first distance, wherein in the second position, the bone plug contacting end surface is adjacent to the bone contacting end surface, wherein the at least partially tube-shaped insertion portion comprises a soft-tissue graft clearance forming a slot through a wall of the at least partially tube-shaped insertion portion, the soft-tissue graft clearance extending from the bone contacting end surface towards the handling portion and allowing soft tissue structures to pass through the soft-tissue graft clearance, and wherein the elongated housing comprises a middle portion, an inside of which is shaped as a partial tube having at least one open side.

2. The bone plug insertion instrument according to claim 1, wherein in the second position, the second distance is less than 1 cm.

3. The bone plug insertion instrument according to claim 1, wherein the bone contacting end surface is oriented at an acute angle relative to the first central axis.

4. The bone plug insertion instrument according to claim 1, wherein the elongated housing comprises a first stop seat, and the elongated plunger comprises a second stop seat, and wherein in the second position, the first and second stop seats are in contact with each other.

5. The bone plug insertion instrument according to claim 1, wherein the elongated plunger defines a second central axis, and wherein a cross section orthogonally to the second central axis of the bone plug contacting end surface is C-shaped, U-shaped, crescent-shaped or semi-circular shaped.

6. The bone plug insertion instrument according to claim 1, wherein the bone plug contacting end surface comprises a rough structure comprising grooves, pointy protrusions, pyramids, a sandpaper-like structure or any combination thereof.

7. The bone plug insertion instrument according to claim 1, wherein the at least partially tube-shaped insertion portion has an inner substantially circular circumference or an inner virtual substantially circular circumference.

8. The bone plug insertion instrument according to claim 1, wherein the at least partially tube-shaped insertion portion comprises a first slot forming a first compliance structure, such as a leaf spring, configured to press the bone plug when received in the space.

9. The bone plug insertion instrument according to claim 8, wherein the elongated plunger comprises an elongated recess sized and shaped to receive the first compliance structure.

10. The bone plug insertion instrument according to claim 1, wherein the bone plug insertion instrument comprises at least one spike protruding from the bone contacting end surface.

11. The bone plug insertion instrument according to claim 1, wherein the elongated housing comprises a second slot extending from the bone contacting end surface a given distance towards the handling portion, and wherein the second slot divides the at least partially tube-shaped insertion portion into a first tube section and a second tube section forming collectively a second compliance structure configured to press the bone plug when received in the space.

12. The bone plug insertion instrument according to claim 1, wherein the elongated housing comprises a rotation-inhibiting protrusion, and wherein the elongated plunger comprises an elongated groove sized and shaped to receive the rotation-inhibiting protrusion, the elongated groove extending parallel or substantially parallel to the first central axis, or wherein the elongated plunger comprises a rotation-inhibiting protrusion, and wherein the elongated housing comprises an elongated groove sized and shaped to receive the rotation-inhibiting protrusion, the elongated groove extending parallel or substantially parallel to the first central axis.

13. The bone plug insertion instrument according to claim 1, wherein the handling portion is formed as an elongated grip.

14. The bone plug insertion instrument according to claim 1, wherein the handling portion is connected to a handle oriented non-parallel to the first central axis.

15. The bone plug insertion instrument according to claim 1, wherein the elongated plunger comprises an impaction surface longitudinally opposite to the bone plug contacting end surface.

16. The bone plug insertion instrument according to claim 1, wherein the elongated housing comprises a friction mechanism configured to press a surface of the elongated plunger to inhibit unwanted movement of the elongated plunger in relation to the elongated housing, or wherein the elongated plunger comprises a friction mechanism configured to press a surface of the elongated housing to inhibit unwanted movement of the elongated plunger in relation to the elongated housing.

17. A method of operating a bone plug insertion instrument for inserting a bone plug into a target bone tunnel, the bone plug insertion instrument comprising:

an elongated housing defining a first central axis, and comprising an at least partially tube-shaped insertion portion, and a handling portion, the at least partially tube-shaped insertion portion defining, substantially orthogonally to the first central axis, an inner cross-sectional area at least partially surrounded by a bone contacting end surface of the at least partially tube-shaped insertion portion; and an elongated plunger comprising an actuating portion and a bone plug driving portion with a bone plug contacting end surface having a contact area of 10% to 90% of the inner cross-sectional area, the elongated plunger being configured to move relative to the elongated housing between a first position and a second, different position, wherein in the first position the bone plug insertion instrument forms an open configuration, in which the bone contacting end surface and the bone plug contacting end surface are separated by a first distance, thereby allowing the bone plug to be received in a space within the at least partially tube-shaped insertion portion between the bone contacting end surface and the bone plug contacting end surface, wherein in the second position, the bone plug insertion instrument forms a substantially closed configuration, in which a second distance between the bone contacting end surface and the bone plug contacting end surface is smaller than the first distance, and wherein in the second position, the bone plug contacting end surface is adjacent to the bone contacting end surface, the method comprising:

retrieving the bone plug using a bone grafting instrument;

inserting the bone plug with an attached tendon into the space inside the at least partially tube-shaped insertion portion between the bone contacting end surface and the bone plug contacting end surface;

pressing the bone plug contacting end surface against the bone plug while the bone plug is within the space;

aligning the bone plug with the target bone tunnel by using the bone plug insertion instrument; and inserting the bone plug into the target bone tunnel by moving the elongated plunger towards the bone contacting end surface to thereby remove the bone plug from the space.

* * * * *